(12) United States Patent
Kloth et al.

(10) Patent No.: US 9,828,312 B2
(45) Date of Patent: Nov. 28, 2017

(54) PROCESS FOR REMOVING OXYGENATES FROM AN OLEFIN STREAM

(71) Applicant: SHELL OIL COMPANY, Houston, TX (US)

(72) Inventors: Antonius Gijsbertus Johannes Kloth, Vaals (NL); Sivakumar Sadasivan Vijayakumari, Gonzales, LA (US); Jeroen Van Westrenen, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 14/439,249

(22) PCT Filed: Oct. 29, 2013

(86) PCT No.: PCT/EP2013/072646
§ 371 (c)(1),
(2) Date: Apr. 29, 2015

(87) PCT Pub. No.: WO2014/067967
PCT Pub. Date: May 8, 2014

(65) Prior Publication Data
US 2015/0291488 A1    Oct. 15, 2015

(30) Foreign Application Priority Data
Oct. 31, 2012   (EP) .................................... 12190705

(51) Int. Cl.
*C07C 1/20* (2006.01)
*C07C 7/11* (2006.01)
*C07C 7/09* (2006.01)

(52) U.S. Cl.
CPC ................ *C07C 7/11* (2013.01); *C07C 1/20* (2013.01); *C07C 7/09* (2013.01); *Y02P 30/42* (2015.11); *Y02P 30/464* (2015.11); *Y02P 30/48* (2015.11)

(58) Field of Classification Search
CPC .......... C07C 11/04; C07C 11/06; C07C 1/20; C07C 7/09; C07C 7/11

USPC ................................ 585/638, 639, 640, 641
See application file for complete search history.

(56) References Cited

U.S. PATENT DOCUMENTS

| 4,567,029 | A | 1/1986 | Wilson et al. |
| 7,323,612 | B2 * | 1/2008 | Egmond .................. C07C 1/20 208/48 Q |
| 7,919,660 | B2 | 4/2011 | Vora et al. |
| 2003/0045655 | A1 | 3/2003 | Hendriksen et al. |
| 2004/0152939 | A1 | 8/2004 | Pettigrew et al. |
| 2005/0033104 | A1 | 2/2005 | van Egmond et al. |
| 2005/0038304 | A1 * | 2/2005 | Van Egmond ............ C07C 1/20 585/324 |
| 2005/0222478 | A1 | 10/2005 | Borgmann et al. |
| 2005/0283038 | A1 | 12/2005 | Kuechler et al. |
| 2006/0004239 | A1 | 1/2006 | Kuechler et al. |
| 2007/0103380 | A1 | 5/2007 | Weste |
| 2007/0155999 | A1 | 7/2007 | Pujado et al. |

FOREIGN PATENT DOCUMENTS

| CN | 101903311 | 8/2013 |
| WO | 03048085 | 6/2003 |
| WO | 2006020083 | 2/2006 |
| WO | 2009045186 | 4/2009 |
| WO | 2009085565 | 7/2009 |

* cited by examiner

*Primary Examiner* — Sharon Pregler

(57) ABSTRACT

The invention removes oxygenate from an olefin rich gas stream, the process comprising:
(a) reacting an oxygenate, in a reaction zone in the presence of a molecular sieve catalyst, at a temperature from 350 to 1000° C., to produce an effluent stream, comprising at least oxygenate, olefin, water and acidic by-products;
(b) cooling the effluent stream and contacting it with a first aqueous stream in a quench zone to produce an aqueous stream and an olefin rich gas stream;
(c) compressing the olefin rich gas stream in one or more compressors in series to produce a compressed gas stream,
(d) cooling the compressed gas stream and separating condensed material from said gas stream after each of the one or more compressors.

9 Claims, 5 Drawing Sheets

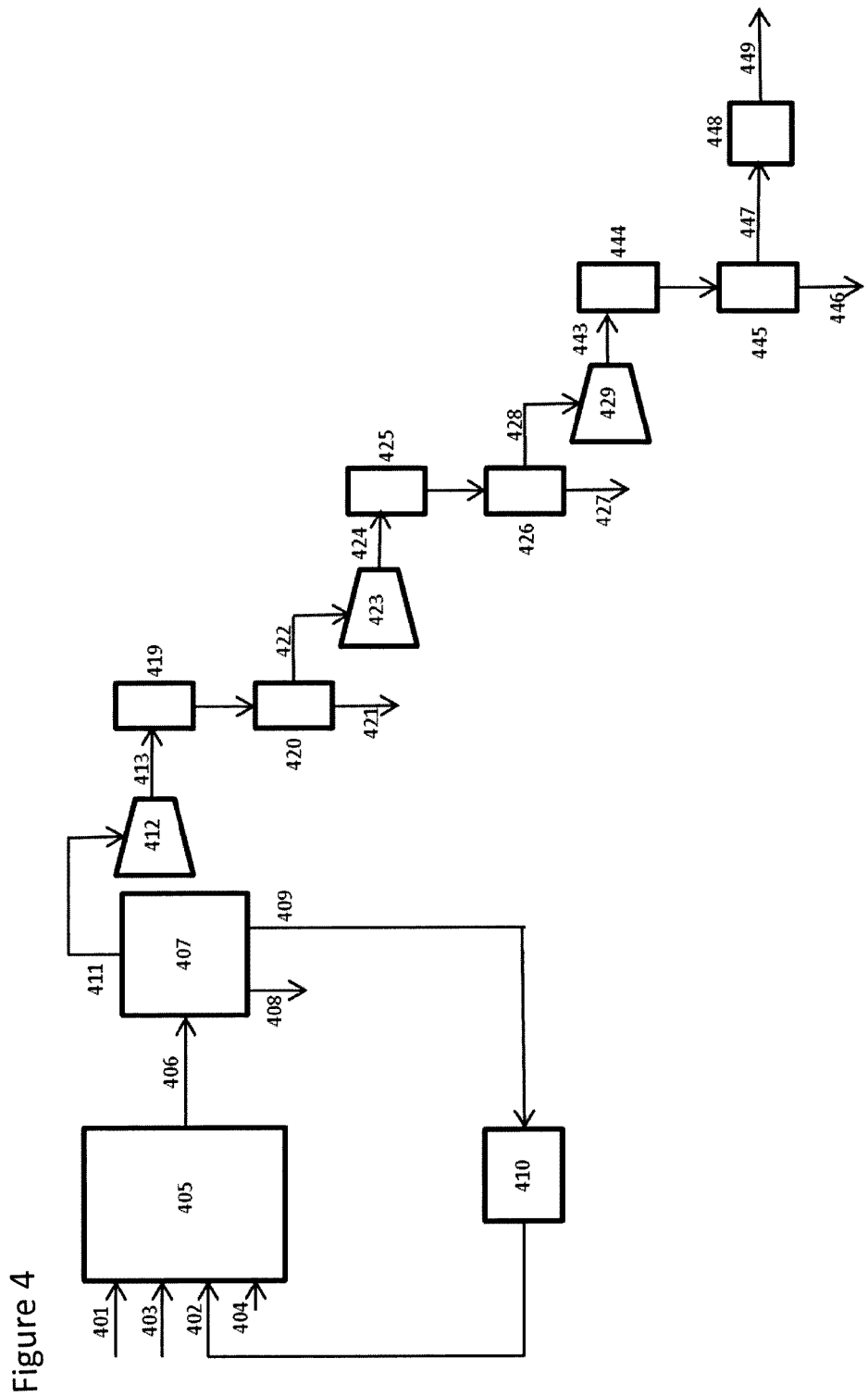

PROCESS FOR REMOVING OXYGENATES FROM AN OLEFIN STREAM

PRIORITY CLAIM

The present application is the National Stage (§371) of International Application No. PCT/EP2013/072646, filed Oct. 29, 2013, which claims priority from European Patent Application No. 12190705.9, filed Oct. 31, 2012 incorporated herein by reference.

FIELD OF THE INVENTION

The present invention relates to a process for removing oxygenates from an olefin stream.

BACKGROUND OF THE INVENTION

Conventionally, ethylene and propylene are produced via steam cracking of paraffinic feedstocks comprising ethane or ethane/propane mixtures, known as gas cracking, or propane, butane, naphtha, NGL (natural gas liquids), condensates, kero, gas oil and hydrowax, known as naphtha cracking. An alternative route to ethylene and propylene is an oxygenate-to-olefin (OTO) process. Interest in OTO processes for producing ethylene and propylene is growing in view of the increasing availability of natural gas. Methane in the natural gas can be converted into, for instance, methanol or dimethylether (DME), both of which are suitable feedstocks for an OTO process.

In an OTO process, an oxygenate such as methanol or dimethylether is provided to a reaction zone of a reactor comprising a suitable conversion catalyst and is converted to ethylene and propylene. In addition to the desired ethylene and propylene, a substantial part of the oxygenate such as methanol is converted to higher hydrocarbons including C4+ olefins, paraffins and carbonaceous deposits on the catalyst. The catalyst is continuously regenerated to remove a portion of the carbonaceous deposits by methods known in the art, for example heating the catalyst with an oxygen-containing gas such as air or oxygen.

The effluent from the reactor, comprising olefins, any unreacted oxygenates such as methanol and dimethylether and other reaction products such as water, once separated from the bulk of the catalyst, is then treated to provide separate component streams. In order to increase the ethylene and propylene yield of the process, the C4+ olefins component stream may be recycled to the reaction zone or alternatively further cracked in a dedicated olefin cracking zone to produce further ethylene and propylene.

Following reaction, the reaction effluent stream is cooled and must be separated into its components, including the desired olefinic products. After initial indirect cooling, for example in a heat exchanger, the reaction effluent stream is contacted with a cooled aqueous stream in a quench zone. Water and most of the oxygenates present will be separated in the quench zone.

However, some of the oxygenates present may be carried over in the olefin rich gas stream from the top of the quench zone. These oxygenates (for example methanol, DME, aldehydes, such as formaldehyde, acetaldehyde and propionaldehyde and ketones, such as methylethylketone) will then need to be removed at a later stage in the separation process to prevent them being present as contaminants in the final product.

In known processes for the production of olefins from oxygenates, the olefin rich gas stream from the quench zone is compressed. The compression is carried out in stages by one or more compressors in series. After each compressor, the compressed gas stream must be cooled and this is usually carried out by indirect heat exchange using an air or water heat exchanger. A separation vessel, such as a knock out drum, is situated after each heat exchanger to separate any condensed materials from the compressed and cooled gas stream. During or after the compression and cooling process, carbon monoxide and carbon dioxide formed as by-products in the OTO reaction zone, are removed from the gas stream in a carbonyl compound removal zone, for example by treating the gas stream with a caustic solution.

The presence of certain oxygenates at this stage can cause problems when treating the gas stream with a caustic solution, as the basic components of the caustic solution, such as hydroxide ions, can catalyse the aldol condensation and subsequent dehydration reactions of particularly acetaldehyde to form unsaturated aldehydes such as acrolein, especially at higher pH, such as a pH of greater than 9. Unsaturated aldehydes will polymerise when allowed to accumulate in the caustic solution and, if the aldol condensation reaction is left unchecked, viscous oily polymers and polymer films and lumbs can be formed. These are known as 'red oil', are insoluble in the caustic solution and can deposit on equipment internals, causing severe fouling and blockages.

In prior art processes, oxygenates remaining in the olefin rich gas stream resulting from the quench zone are usually removed using an alcohol, usually methanol, wash or by extractive distillation with an alcohol. These processes take place after at least one complete compression stage comprising compression, cooling in a heat exchanger and separation of condensed material. Examples of alcohol wash processes in the prior art can be found in US 2005/0033104, US 2005/0222478, US 2006/0004239 and US 2005/0283038. An extractive distillation process is described in US 2003/0045655.

It would be desirable to provide a simple, integrated process for the removal of oxygenates from the olefin rich gas stream produced in the quench zone and the cooling of said gas stream.

SUMMARY OF THE INVENTION

Accordingly, the present invention provides a process for the removal of oxygenates from an olefin rich gas stream, the process comprising the steps of:
(a) reacting an oxygenate feedstock, comprising oxygenate, in an oxygenate reaction zone in the presence of a catalyst comprising a molecular sieve, at a temperature in the range of from 350 to 1000° C., to produce a reaction effluent stream, comprising at least oxygenates, olefins, water and acidic by-products;
(b) cooling the reaction effluent stream and contacting it with a first aqueous stream in a quench zone to produce an aqueous stream and an olefin rich gas stream;
(c) compressing the olefin rich gas stream in one or more compressors in series to produce a compressed gas stream,
(d) cooling the compressed gas stream and separating condensed material from said gas stream after each of the one or more compressors,
wherein after at least one of the one or more compressors in step (c), step (d) is carried out by contacting the compressed gas stream directly with a second aqueous stream and separating the resultant material into an oxygenates depleted gas stream and an aqueous wash stream.

BRIEF DESCRIPTION OF THE DRAWINGS

FIG. 4 is a schematic diagram of an example of a prior art process.

DETAILED DESCRIPTION OF THE INVENTION

Figure 1:
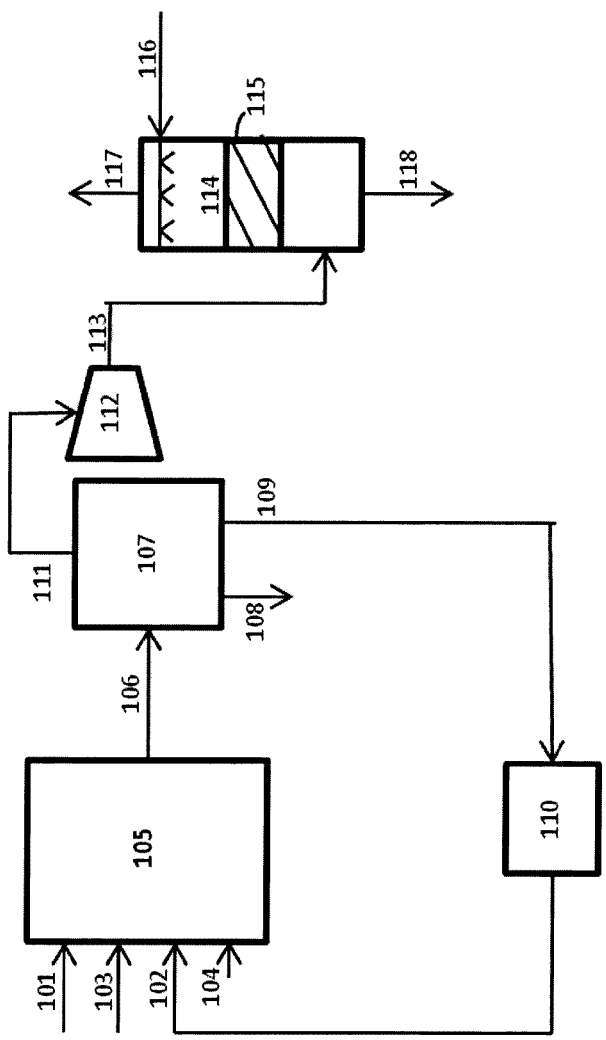
FIGS. 1 to 3 are schematic diagrams of exemplary, but non-limiting, embodiments of a process for removal of oxygenates from an olefin rich gas stream as described herein.

The present invention provides a process for the removal of oxygenates from an olefin rich gas stream resulting from a quench zone in an OTO process. The removal of oxygenates is achieved during the process of compressing said olefin rich gas stream. In the present invention, after at least one of the one or more compressors used in the compression process, the resultant compressed gas is directly contacted with an aqueous stream. Contacting the compressed gas directly with an aqueous stream achieves the dual effects of cooling the compressed gas and removing oxygenates present therein. This is in contrast to prior art processes, wherein after each compressor the resultant compressed gas is cooled using an indirect heat exchanger and then condensed materials are separated in, for example, a knock-out drum, with oxygenates being removed in a separate step. The process of the present invention also provides direct cooling to the olefin rich gas, a more efficient process than the indirect cooling provided in the prior art. Thus, the process of the present invention provides a simple and integrated process for the removal of oxygenates from an olefin rich gas stream at the same time as cooling said gas stream.

Another benefit is that the direct quench system can be designed for a very high turndown which is much higher than for a heat exchanger.

The olefin rich gas stream from the quench zone is compressed in one or more compressors in series. Preferably, two or more compressors, more preferably three or more compressors are used in series.

Suitably, the process of contacting the compressed gas stream directly with a second aqueous stream can take place after any of the one or more compressors in series. Therefore, if one compressor is used, the process of contacting the compressed gas stream directly with a second aqueous stream takes place after that compressor. If two compressors are used in series, the process of contacting the compressed gas stream directly with a second aqueous stream may take place after the first compressor, after the second compressor or after both compressors, preferably after the second compressor. If three compressors are used, the process of contacting the compressed gas stream directly with a second aqueous stream may take place after the first compressor, after the second compressor, after the third compressor or after more than one of the compressors, preferably after the third compressor. If four compressors are used, the process of contacting the compressed gas stream directly with a second aqueous stream may take place after the first compressor, after the second compressor, after the third compressor, after the fourth compressor or after more than one of the compressors, preferably after the second or third compressor. If five compressors are used, the process of contacting the compressed gas stream directly with a second aqueous stream may take place after the first compressor, after the second compressor, after the third compressor, after the fourth compressor, after the fifth compressor or after more than one of the compressors, preferably after the second or third compressor.

Preferably, for process simplicity, the process of contacting the compressed gas stream directly with a second aqueous stream takes place after only one of the compressors.

In one embodiment, the second aqueous stream is injected directly into a pipe or other conduit transporting the compressed gas stream from the compressor.

In one embodiment, spray nozzles are located in the sides of the conduit such that the second aqueous stream is injected directly into the conduit transporting the compressed gas stream.

Preferably, the process of contacting the compressed gas stream directly with a second aqueous stream takes place at a stage where the gas stream has been compressed to a pressure in the range of from 9 to 15 bar absolute (900 to 1500 kPa), more preferably in the range of from 10 to 12 bar absolute (1000 to 1200 kPa).

Carbonyl compounds such as carbon monoxide and carbon dioxide are removed from the gas stream in a carbonyl compound removal zone for example by treating the gas stream with a caustic solution. Although the gas stream may be treated in the carbonyl compound removal zone before any compression occurs, it is preferable that it is treated in the carbonyl compound removal zone after being compressed in at least one of the one or more compressors. More preferably, the gas stream is treated in the carbonyl compound removal zone after being compressed by at least two, more preferably by at least three compressors. Suitably, one or more further compressors are used after the carbonyl compound removal zone.

Preferably, the process of contacting the compressed gas stream directly with a second aqueous stream is carried out before the gas stream is treated in the carbonyl compound removal zone. This has the added advantage of reducing red oil make in the carbonyl compound removal zone.

When more than one compressor is present and the process of contacting the compressed gas stream directly with a second aqueous stream does not take place after each of the compressors, it is suitable for a prior art process for cooling the compressed gas stream and separating condensed material to be used after the other compressors. Thus, after these compressors, the compressed gas stream will be cooled by known means, e.g. an air or water or process stream cooled heat exchanger and then condensed material will be separated by known means, e.g. in a knock out drum.

Suitably, the second aqueous stream may be contacted with the compressed gas stream in a column. Said column may contain trays or packing. Preferably, said column contains packing. The compressed gas stream may be introduced into the column at a point below the level of any packing and will, thus, travel upwards through the column and through any packing. The second aqueous stream may be introduced to the column above the packing and will travel downwards through the column, contacting the compressed gas stream in a counter-current manner. The resultant oxygenate depleted olefin rich gas stream can then be removed at the top of the column and the aqueous wash stream removed at the bottom of the column.

The second aqueous stream comprises more than 60 wt % water. Preferably the second aqueous stream comprises at least 70 wt %, more preferably at least 80 wt %, even more preferably at least 90 wt %, most preferably at least 95 wt % water.

The molar ratio of water in the second aqueous stream to gas in the gas stream is preferably no more than 10:1, more preferably no more than 5:1, even more preferably no more than 3:1, most preferably no more than 2:1. The molar ratio of water in the second aqueous stream to gas in the gas stream is preferably at least 1:2, more preferably at least 1:1.5, most preferably at least 1:1.2.

Suitably, the second aqueous stream contains a lower content of at least one of the oxygenates present than the compressed gas stream. Preferably, the second aqueous stream contains no more than 5000 ppm oxygenates, more preferably no more than 100 ppm oxygenates, even more preferably no more than 50 ppm oxygenates, even more preferably no more than 10 ppm, even more preferably no more than 5 ppm oxygenates, most preferably no more than 1 ppm oxygenates, wherein oxygenates refers to all oxygenates present.

The olefin rich gas stream exiting the quench zone typically comprises no more than 20 wt % oxygenates, preferably no more than 10 wt % oxygenates. Said olefin rich gas stream preferably comprises at least 1 wt % oxygenates, preferably at least 5 wt % oxygenates. The olefin rich gas stream exiting the quench zone typically comprises at least 50 wt %, preferably at least 60 wt %, more preferably at least 70 wt % olefins.

The oxygenates depleted gas stream will preferably comprise no more than 5%, more preferably no more than 2 wt %, even more preferably no more than 1, even more preferably no more than 0.5, most preferably no more than 0.2 wt % of the oxygenates present in the olefin rich gas stream on a weight basis.

The aqueous wash stream formed in the process of the present invention is preferably recycled and re-used in the overall process. In one preferred embodiment of the invention, it may be combined with aqueous material from the quench zone. The oxygenates present may then be separated and recycled to the OTO reaction zone and the water reused in another part of the process.

The temperature of the olefin rich gas stream exiting the quench zone is suitable in the range of from 20 to 50° C., preferably in the range of from 20 to 40° C.

After compressing the olefin rich gas stream, the resultant compressed gas stream will typically be at a temperature in the range of from 75 to 100° C., preferably in the range of from 80 to 95° C. and must be cooled to a temperature of no more than 55° C., preferably no more than 50° C., more preferably no more than 45° C., most preferably no more than 40° C.

After the process of the present invention, the oxygenates depleted gas stream will be further processed to separate it into its constituent parts. This can be achieved by any suitable process known in the art.

Reference herein to an oxygenate feedstock is to an oxygenate-comprising feedstock. In the oxygenate (or OTO) reaction zone, at least part of the feedstock is converted into a product containing one or more olefins, preferably including lower olefins, in particular ethylene and typically propylene.

The oxygenate used in the process is preferably an oxygenate which comprises at least one oxygen-bonded alkyl group. The alkyl group preferably is a C1-C5 alkyl group, more preferably C1-C4 alkyl group, i.e. comprises 1 to 5 or 1 to 4 carbon atoms respectively; more preferably the alkyl group comprises 1 or 2 carbon atoms and most preferably one carbon atom. Examples of oxygenates that can be used in the oxygenate feedstock include alcohols and ethers. Examples of preferred oxygenates used in the oxygenate feedstock include alcohols, such as methanol, ethanol, propanol; and dialkyl ethers, such as dimethyl ether, diethyl ether, methylethyl ether. Preferably, the oxygenate is methanol or dimethyl ether, or a mixture thereof.

Preferably, the oxygenate feedstock comprises at least 50 wt % of oxygenate, in particular methanol and/or dimethyl ether, based on total hydrocarbons, more preferably at least 70 wt %.

An oxygenate co-feed, comprising oxygenate recovered or produced in the process downstream of step (d) of the process of the present invention, such as an oxygenate recovered stream, may also be supplied, as discussed below. Such a stream may contain methanol, dimethyl ether and/or MTBE.

A diluent, such as water or steam, may also be provided to the oxygenate reaction zone. The molar ratio of oxygenate to diluent may be between 10:1 and 1:10, preferably between 4:1 and 1:2, in particular when the oxygenate is methanol and the diluent is water (typically steam).

Preferably, in addition to the oxygenate and diluent, an olefinic co-feed is provided along with and/or as part of the oxygenate feedstock. Reference herein to an olefinic co-feed is to an olefin-comprising co-feed.

The olefinic co-feed preferably comprises C4+ olefins i.e. C4 and higher olefins, more preferably C4 and C5 olefins.

In one preferred embodiment of the present invention, the olefinic co-feed comprises at least 30 wt %, preferably at least 50 wt %, more preferably at least 70 wt % of C4 hydrocarbon species. In this embodiment, the remainder of the olefinic co-feed comprises at least 70 wt %, more preferably at least 80 wt %, even more preferably at least 90 wt % C5 hydrocarbon species.

In a second preferred embodiment of the present invention, the olefinic co-feed comprises at least 50 wt %, preferably at least 70 wt % of C5 hydrocarbon species. In this embodiment, the remainder of the olefinic co-feed comprises at least 70 wt %, more preferably at least 80 wt %, even more preferably at least 90 wt % C4 hydrocarbon species.

Of the C4 hydrocarbon species present in the olefinic co-feed, preferably at least 35 wt %, more preferably at least 50 wt %, more preferably at least 75 wt % are olefins.

Of the C5 hydrocarbon species present in the olefinic co-feed, preferably at least 30 wt %, more preferably at least 45 wt % are non-cyclic olefins.

In order to maximize production of ethylene and propylene, it is desirable to maximize the recycle of C4 olefins in the effluent of the OTO process. This can be done by recycling at least part of the C4+ hydrocarbon fraction, preferably C4-C5 hydrocarbon fraction, more preferably C4 hydrocarbon fraction, in the OTO effluent. However, a certain part thereof, such as between 1 and 5 wt %, can be withdrawn as purge, since otherwise saturated hydrocarbons, in particular C4s (normal and iso butane) may build up in the process, which are substantially not converted under the OTO reaction conditions. Preferably, at least 70 wt % of the olefinic co-feed, during normal operation, is formed by a recycle stream of a C4+ hydrocarbon fraction from the OTO reaction effluent. Preferably, at least 90 wt % of olefinic co-feed, based on the whole olefinic co-feed, is formed by such recycle stream.

The preferred molar ratio of oxygenate in the oxygenate feedstock to olefin in the olefinic co-feed provided to the oxygenate reaction zone depends on the specific oxygenate used and the number of reactive oxygen-bonded alkyl groups therein. Preferably the molar ratio of oxygenate to olefin in the total feed lies in the range of 20:1 to 1:10, more preferably in the range of 18:1 to 1:5, still more preferably in the range of 15:1 to 1:3, even still more preferably in the range of 12:1 to 1:3.

A variety of OTO processes are known for converting oxygenates, such as for instance methanol or dimethyl ether to an olefin-containing product, as already referred to above. One such process is described in WO 2006/020083. Processes integrating the production of oxygenates from synthesis gas and their conversion to light olefins are described in US 20070203380 and US 20070155999.

Catalysts suitable for converting the oxygenate feedstock comprise molecular sieve. Such molecular sieve-comprising catalysts typically also include binder materials, matrix material and optionally fillers. Suitable matrix materials include clays, such as kaolin. Suitable binder materials include silica, alumina, silica-alumina, titania and zirconia, wherein silica is preferred due to its low acidity.

Molecular sieves preferably have a molecular framework of one, preferably two or more corner-sharing tetrahedral units, more preferably, two or more $[SiO_4]$, $[AlO_4]$ and/or $[PO_4]$ tetrahedral units. These silicon, aluminum and/or phosphorus based molecular sieves and metal containing silicon, aluminum and/or phosphorus based molecular sieves have been described in detail in numerous publications including for example, U.S. Pat. No. 4,567,029. In a preferred embodiment, the molecular sieves have 8-, 10- or 12-ring structures and an average pore size in the range of from about 3 Å to 15 Å.

Suitable molecular sieves are silicoaluminophosphates (SAPO), such as SAPO-17, -18, 34, -35, -44, but also SAPO-5, -8, -11, -20, -31, -36, 37, -40, -41, -42, -47 and -56; aluminophosphates (AlPO) and metal substituted (silico) aluminophosphates (MeAlPO), wherein the Me in MeAlPO refers to a substituted metal atom, including metal selected from one of Group IA, IIA, IB, IIIB, IVB, VB, VIB, VIIB, VIIIB and Lanthanides of the Periodic Table of Elements. Preferably, the substituted metal atom (Me) is selected from one of the group consisting of Co, Cr, Cu, Fe, Ga, Ge, Mg, Mn, Ni, Sn, Ti, Zn and Zr.

Alternatively, the conversion of the oxygenate feedstock may be accomplished by the use of an aluminosilicate-comprising catalyst, in particular a zeolite-comprising catalyst. Suitable catalysts include those containing a zeolite of the ZSM group, in particular of the MFI type, such as ZSM-5, the MTT type, such as ZSM-23, the TON type, such as ZSM-22, the MEL type, such as ZSM-11, and the FER type. Other suitable zeolites are for example zeolites of the STF-type, such as SSZ-35, the SFF type, such as SSZ-44 and the EU-2 type, such as ZSM-48.

Aluminosilicate-comprising catalyst, and in particular zeolite-comprising catalyst are preferred when an olefinic co-feed is fed to the oxygenate conversion zone together with oxygenate, for increased production of ethylene and propylene.

Preferred catalysts comprise a more-dimensional zeolite, in particular of the MFI type, more in particular ZSM-5, or of the MEL type, such as zeolite ZSM-11. Such zeolites are particularly suitable for converting olefins, including iso-olefins, to ethylene and/or propylene. The zeolite having more-dimensional channels has intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably, the channels in at least one of the directions are 10-membered ring channels. A preferred MFI-type zeolite has a silica-to-alumina ratio, SAR, of at least 60, preferably at least 80. More preferred MFI-type zeolites have a silica-to-alumina ratio in the range of from 60 to 150, more preferably of from 80 to 100, Particular catalysts include catalysts comprising one or more zeolites having one-dimensional 10-membered ring channels, i.e. one-dimensional 10-membered ring channels, which are not intersected by other channels. Preferred examples are zeolites of the MTT and/or TON type. Preferably, the catalyst comprises at least 40 wt %, preferably at least 50 wt %. of such zeolites based on total zeolites in the catalyst. In one embodiment, the catalyst comprises in addition to one or more one-dimensional zeolites having 10-membered ring channels, such as of the MTT and/or TON type, a more-dimensional zeolite, in particular of the MFI type, more in particular ZSM-5, or of the MEL type, such as zeolite ZSM-11.

The catalyst may further comprise phosphorus as such or in a compound, i.e. phosphorus other than any phosphorus included in the framework of the molecular sieve. It is preferred that a MEL or MFI-type zeolite comprising catalyst additionally comprises phosphorus. The phosphorus may be introduced by pre-treating the MEL or MFI-type zeolites prior to formulating the catalyst and/or by post-treating the formulated catalyst comprising the MEL or MFI-type zeolites. Preferably, the catalyst comprising MEL or MFI-type zeolites comprises phosphorus as such or in a compound in an elemental amount of from 0.05 to 10 wt % based on the weight of the formulated catalyst. A particularly preferred catalyst comprises phosphorus and MEL or MFI-type zeolite having SAR of in the range of from 60 to 150, more preferably of from 80 to 100. An even more particularly preferred catalyst comprises phosphorus and ZSM-5 having SAR of in the range of from 60 to 150, more preferably of from 80 to 100.

It is preferred that molecular sieves in the hydrogen form are used in the oxygenate conversion catalyst, e.g., HZSM-22, HZSM-23, and HZSM-48, HZSM-5. Preferably at least 50% w/w, more preferably at least 90% w/w, still more preferably at least 95% w/w and most preferably 100% of the total amount of molecular sieve used is in the hydrogen form. It is well known in the art how to produce such molecular sieves in the hydrogen form.

The reaction conditions of the oxygenate conversion, include a reaction temperature of 350 to 1000° C., preferably from 350 to 750° C., more preferably 450 to 700° C., even more preferably 500 to 650° C.; and a pressure from 0.1 kPa (1 mbar) to 5 MPa (50 bar), preferably from 100 kPa (1 bar) to 1.5 MPa (15 bar).

Preferably, the oxygenate feedstock is preheated to a temperature in the range of from 200 to 550° C., more preferably 250 to 500° C. prior to contacting with the molecular sieve-comprising catalyst.

The catalyst particles used in the process can have any shape known to the skilled person to be suitable for this purpose, and can be present in the form of spray dried catalyst particles, spheres, tablets, rings, extrudates, etc. Extruded catalysts can be applied in various shapes, such as, cylinders and trilobes. Spray-dried particles allowing use in a fluidized bed or riser reactor system are preferred. Spherical particles are normally obtained by spray drying. Preferably the average particle size is in the range of 1-200 µm, preferably 50-100 µm.

Although the C4+ hydrocarbon fraction in the reaction effluent may be recycled as an olefinic co-feed as discussed above, in an alternative embodiment, at least part of the olefins in the C4+ hydrocarbon fraction are converted to ethylene and/or propylene by contacting the C4+ hydrocarbon fraction in a separate unit with a molecular sieve-comprising catalyst, particularly a zeolite-comprising catalyst. This is particularly preferred where molecular sieve-comprising catalyst in the OTO process comprises a least one SAPO, AlPO, or MeAlPO type molecular sieve, preferably SAPO-34. These catalysts are less suitable for converting C4+ olefins.

Preferably, the C4+ hydrocarbon fraction is contacted with the zeolite-comprising catalyst at a reaction temperature of 350 to 1000° C., preferably from 375 to 750° C., more preferably 450 to 700° C., even more preferably 500 to 650° C.; and a pressure from 0.1 kPa (1 mbar) to 5 MPa (50 bar), preferably from 100 kPa (1 bar) to 1.5 MPa (15 bar).

Optionally, the stream comprising C4+ olefins also contains a diluent. Examples of suitable diluents include, but are not limited to, liquid water or steam, nitrogen, argon, paraffins and methane. Under these conditions, at least part of the olefins in the C4+ hydrocarbon fraction are converted to further ethylene and/or propylene. The further ethylene and/or propylene may be combined with the further ethylene and/or propylene obtained directly from the oxygenate reaction zone. Such a separate process step directed at converting C4+ olefins to ethylene and propylene is also referred to as an olefin cracking process (OCP).

Catalysts comprising molecular sieve, particularly aluminosilicate-comprising catalysts, and more particularly zeolite-comprising catalysts, have the further advantage that in addition to the conversion of methanol or ethanol, these catalysts also induce the conversion of olefins to ethylene and/or propylene. Therefore, aluminosilicate-comprising catalysts, and in particular zeolite-comprising catalysts, are particularly suitable for use as the catalyst in an OCP. Particular preferred catalysts for the OCP reaction, i.e. converting part of the olefinic product, and preferably part of the C4+ hydrocarbon fraction of the olefinic product including C4+ olefins, are catalysts comprising at least one zeolite selected from MFI, MEL, TON and MTT type zeolites, more preferably at least one of ZSM-5, ZSM-11, ZSM-22 and ZSM-23 zeolites.

Both the OTO process and the OCP may be operated in a fluidized bed or moving bed, e.g. a fast fluidized bed or a riser reactor system, and also in a fixed bed reactor or a tubular reactor. A fluidized bed or moving bed, e.g. a fast fluidized bed or a riser reactor system are preferred.

The catalyst can deactivate in the course of the OCP and OTO process. The deactivation occurs primarily due to deposition of carbonaceous deposits, such as coke, on the catalyst by side reactions. The deactivated catalyst can be regenerated to remove a portion of the carbonaceous deposit by methods known in the art. It is not necessary, and indeed may be undesirable, to remove all the carbonaceous deposit from the catalyst as it is believed that a small amount of residual carbonaceous deposit such as coke may enhance the catalyst performance. Additionally, it is believed that complete removal of the carbonaceous deposit may also lead to degradation of the molecular sieve.

The same catalyst may be used for both the OTO process and OCP. In such a situation, the catalyst comprising molecular sieve, particularly comprising aluminosilicate molecular sieve and more particularly comprising zeolite, may be first used in the OCP reaction zone for the conversion of the C4+ olefins of the C4+ hydrocarbon fraction. The catalyst from the OCP may then be used, typically without regeneration, in the OTO process for conversion of an oxygenate feedstock and an olefinic co-feed. The deactivated catalyst from the OTO process may then be regenerated as described herein, and the regenerated catalyst then used again in the OCP.

This line-up may be beneficial because it provides good heat integration between the OCP, OTO and regeneration processes. The OCP is endothermic and at least a portion of the heat of reaction can be provided by passing catalyst from the regeneration zone to the OCP reaction zone, because the regeneration reaction which oxidizes the carbonaceous deposits from the loaded catalyst is exothermic.

Embodiments of the present invention will now be described by way of example only and with reference to the accompanying non-limiting figures.

FIG. 1 exemplifies an embodiment of the present invention. An oxygenate feedstock 101 is fed into the oxygenate reaction zone 105. An oxygenate co-feed 102 may also be supplied by an oxygenate recycle stream. A diluent 103 may also be provided to the reaction zone. Preferably, an olefinic co-feed 104 is also provide to the reaction zone. The oxygenate co-feed, diluent and olefinic co-feed may be supplied to the reaction zone separately or one or more of these streams may be combined with the oxygenate feedstock or together before being fed to the reaction zone.

In the oxygenate (or OTO) reaction zone 105, reaction is carried out in the presence of a catalyst at a temperature in the range of from 350 to 1000° C. Following reaction, the gaseous product is separated from the bulk of the catalyst to produce a reaction effluent stream 106, which is passed to quench zone 107. In the quench zone, an oxygenate containing aqueous stream 109 is produced and can be subjected to separation and purification in the oxygenate separation zone 110 before being recycled as the oxygenate co-feed 102. A solid stream 108 is also produced.

The olefin rich gas stream 111 from the quench zone comprises olefins and oxygenate and is compressed in a compressor 112. The compressed gas stream 113 is the contacted with a second aqueous stream 116 in a column 114 containing packing 115. An oxygen depleted gas stream 117 is removed from the top of the column and an aqueous wash stream 118 is removed from the bottom of the column. The aqueous wash stream may then be combined with stream 109 for recovery of the oxygenate contained therein. The water produced in the oxygenate separation zone 110 may be recycled in the overall process (not shown in FIG. 1).

Figure 2:
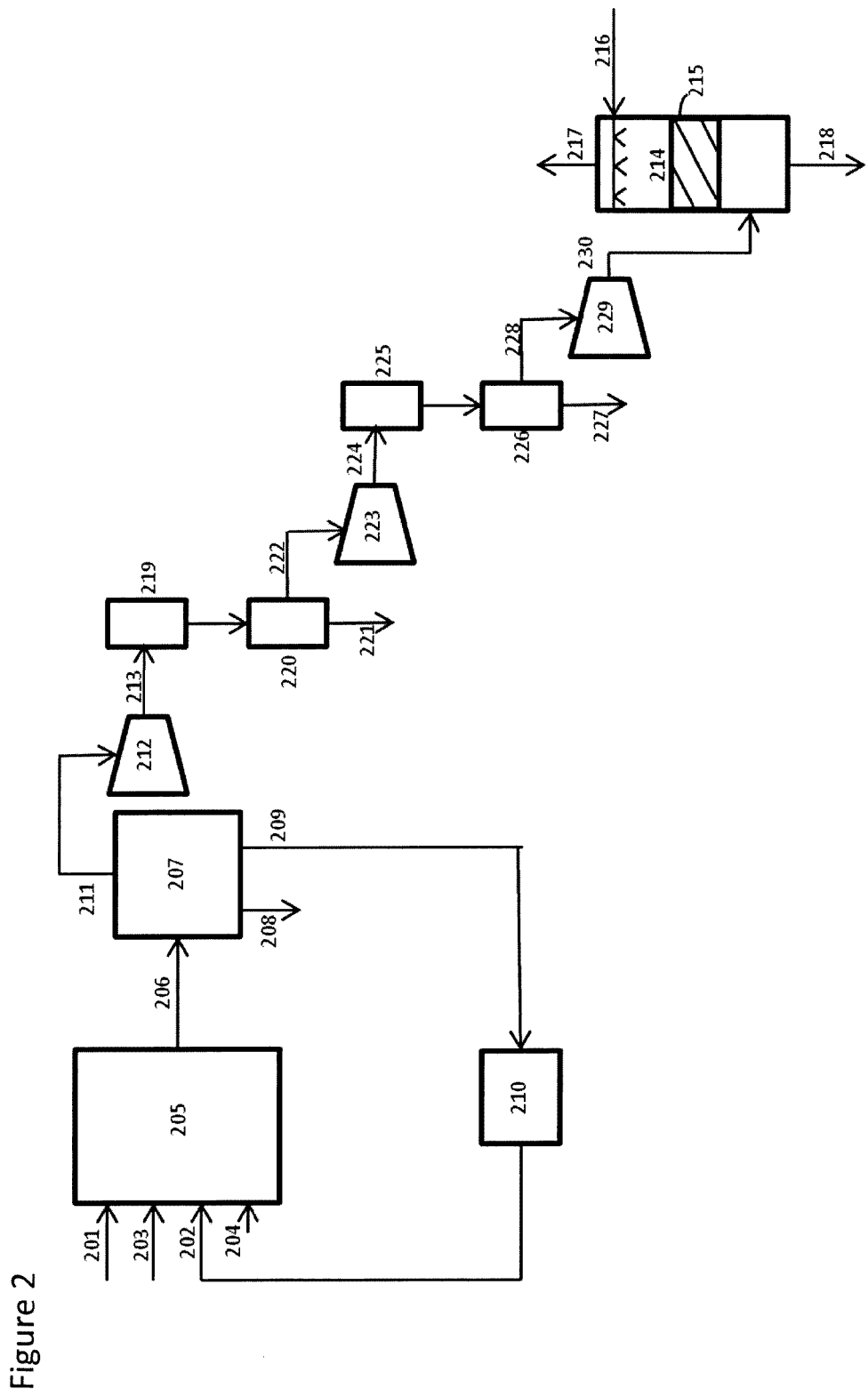

FIG. 2 shows a preferred embodiment of the present invention, wherein 3 compressors are used and the compressed gas stream is contacting with a second aqueous stream after only the third compressor.

As in FIG. 1, in the oxygenate (or OTO) reaction zone 205, reaction is carried out in the presence of a catalyst at a temperature in the range of from 350 to 1000° C. Following reaction, the gaseous product is separated from the bulk of the catalyst to produce a reaction effluent stream 206, which is passed to quench zone 207. In the quench zone, an oxygenate containing aqueous stream 209 is produced and can be subjected to separation and purification in the oxygenate separation zone 210 before being recycled as the oxygenate co-feed 202. A solid stream 208 is also produced.

The olefin rich gas stream 211 from the quench zone comprises olefins and oxygenate and is compressed in a first compressor 212. The first compressed gas stream 213 is then cooled in a heat exchanger 219 before being passed to a separator or knock out drum 220, where condensable materials 221 are separated. A first compressed olefin rich gas stream 222 is then compressed in a second compressor 223. The second compressed gas stream 224 is cooled in a heat exchanger 225 before being passed to a separator or knock out drum 226, where condensable materials 227 are separated. A second compressed olefin rich gas stream 228 is then compressed in a third compressor 229.

The third compressed gas stream 230 is the contacted with a second aqueous stream 216 in a column 214 containing packing 215. An oxygen depleted gas stream 217 is removed from the top of the column and an aqueous wash stream 218 is removed from the bottom of the column. The aqueous wash stream may then be combined with stream 209 for recovery of the oxygenate contained therein. The water produced in the oxygenate separation zone 210 may be recycled in the overall process (not shown in FIG. 2).

Figure 3:
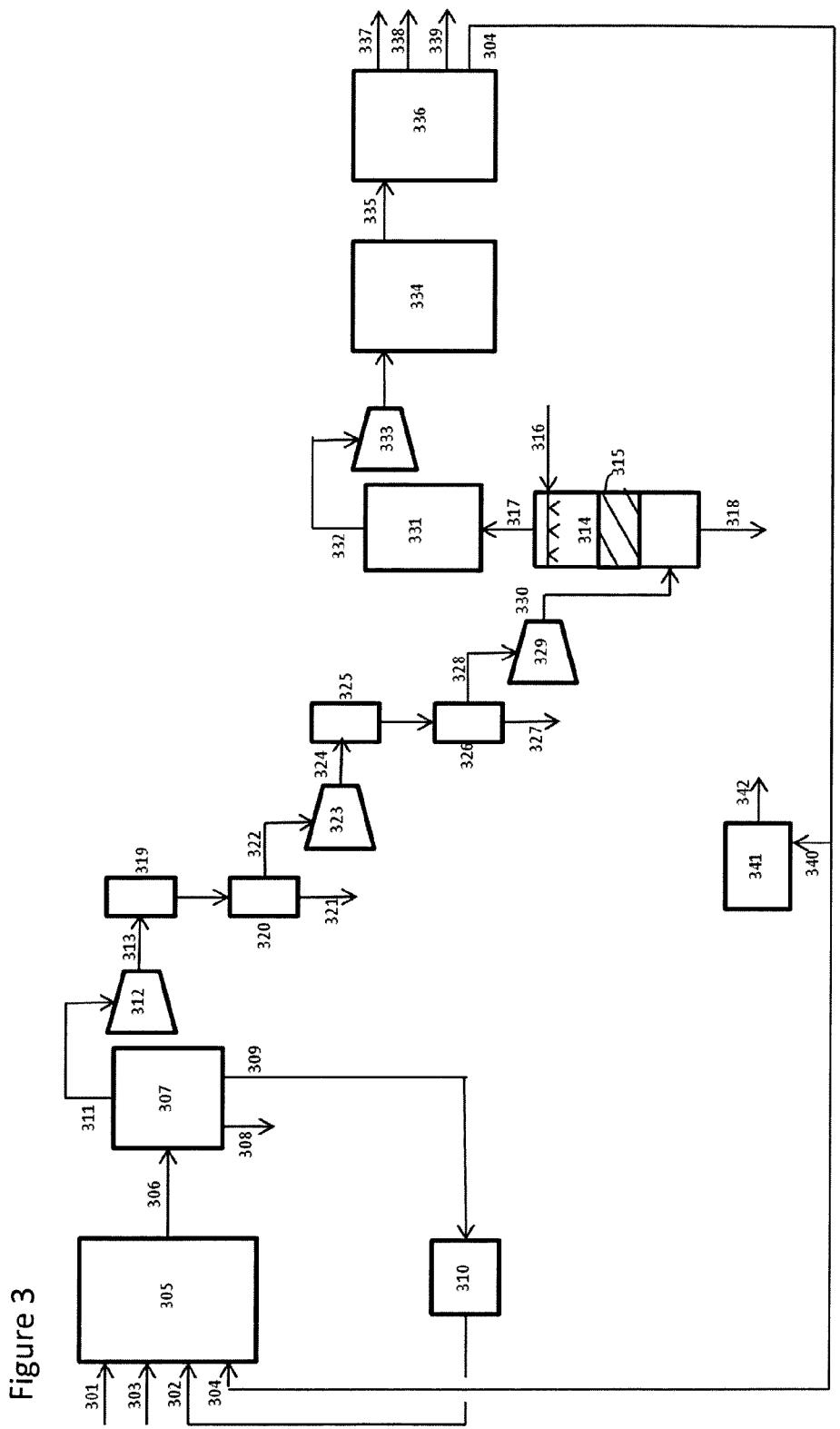

FIG. 3 shows one possible embodiment of the invention as it is incorporated into an overall process for the production of olefinic products such as ethylene and propylene. The process is carried out as described for FIG. 2. It should be noted that as used herein in the numbers on the diagrams, the first digit refers to the Figure number. Thus, numbers 204 and 304 will refer to the same feature in FIGS. 2 and 3, respectively.

The oxygenate depleted gas stream 317 is then passed to a carbonyl compound absorption zone 331 in which the stream is treated with a caustic solution to remove carbon dioxide and carbonyl compounds. The resultant stream 332 is further compressed in one or more compressors 333 before being passed to water removal zone 334. After water removal, the remaining gas stream 335 enters an olefin separation zone 336 to be separated, preferably by one or more cryogenic distillation processes, to provide two or more olefinic component streams 337, 338, 339 and 304, including a stream comprising C4+ olefins which is recycled as olefinic co-feed 304.

In one alternative embodiment, all or part 340 of this stream is subjected to an OCP 341 to provide a stream comprising ethylene and propylene 342. This stream 342 can then be fed back into the process as part of olefin rich gas stream 311.

Figure 5B:
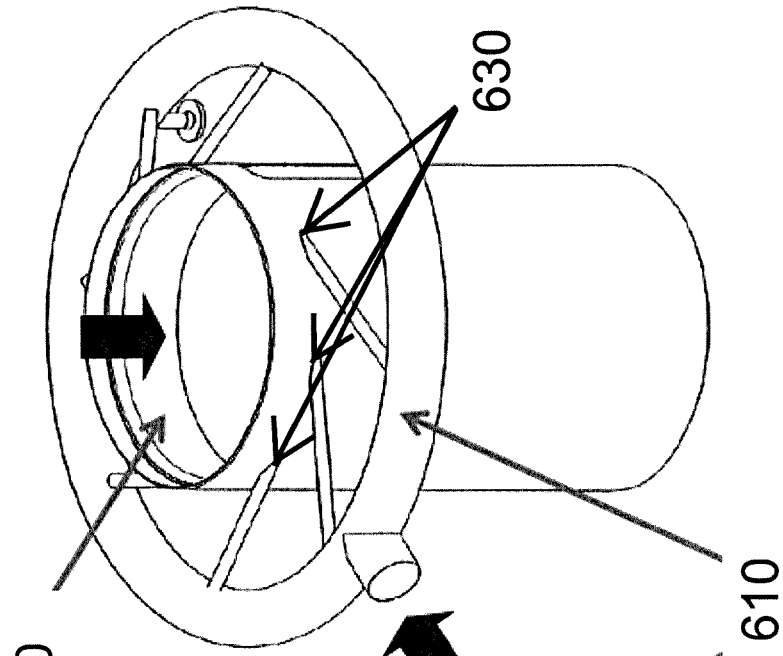
FIG. 5 provides 2 views (5A and 5B) of an embodiment of a quench fitting.
Figure 5A:
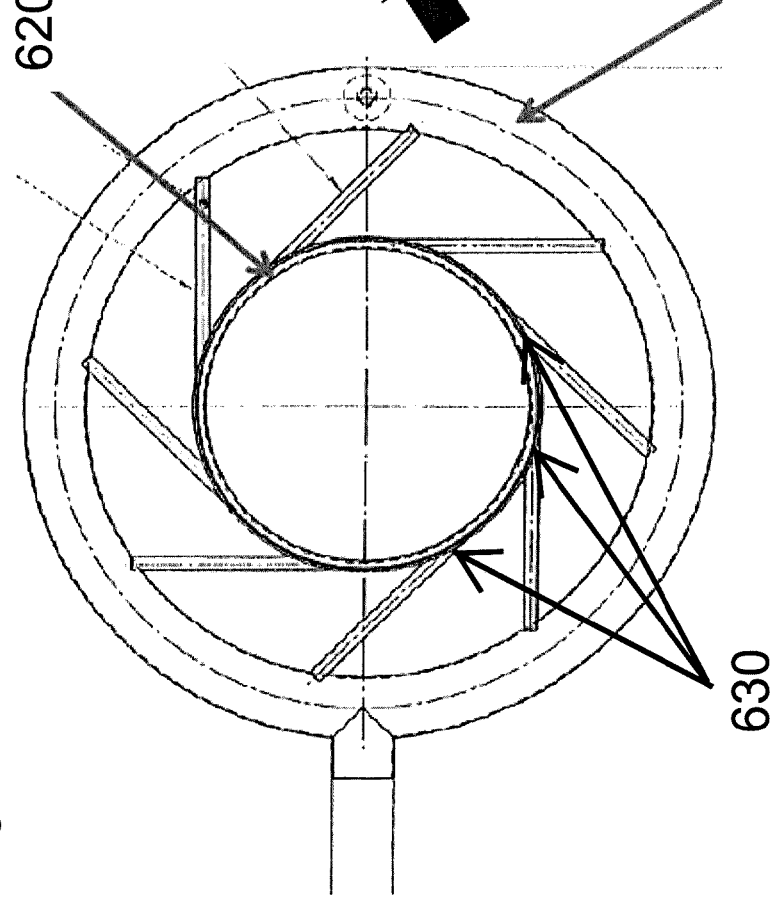

FIG. 5 uses a different numbering scheme than FIGS. 1-4 and the items in this Figure are not related by number to any of the previous Figures. FIG. 5 depicts an embodiment of a direct quench fitting with two views, 5A and 5B. FIG. 5A shows a top view of a direct quench fitting. The quench ring 610 is concentric to the effluent conduit 620 and the direct quench points 630 are located at a plurality of points around the effluent conduit. The direct quench points may be spray nozzles or another type of injection device for injecting the aqueous liquid into the effluent conduit FIG. 5B shows a side view of the quench ring 610, the effluent conduit 620 and the direct quench points 630.

EXAMPLE

The process of the invention was modelled using an ASPEN simulation of a process set up as exemplified in FIG. 2 with a molar ratio of water in the second aqueous stream to gas in the compressed gas stream of 1:1. An ASPEN simulation of a process set up as exemplified in FIG. 4 was also run to provide comparison data. FIG. 4 shows a process in which the same steps are followed as in FIG. 2 until after the third compressor 429. In FIG. 4, after the third compressor 429, the third compressed gas stream 443 is cooled in a heat exchanger 444 before being passed to a separator or knock out drum 445, where condensable materials 446 are separated. Gas stream 447 is then further cooled in a heat exchanger 448 to produce stream 449. Such a set-up is typical of prior art processes.

In Table 1 below, the contents of certain oxygenates in each of stream 406, 449, 230 and 217, as calculated in the ASPEN simulation, are shown. Also given is the amount of each oxygenate removed by the water wash in the process shown in FIG. 2.

This simulation shows almost total removal of formaldehyde and methanol as well as removal of considerable amounts of other oxygenates when using the process of the present invention.

TABLE 1

| Oxygenate Component | 406 mole flow kmol/hr | 449 mole flow kmol/hr | 230 Mole flow kmol/hr | 217 mole flow kmol/hr | Amount removed by water (%) |
|---|---|---|---|---|---|
| DME | 3.123 | 3.136 | 3.191 | 3.144 | 2.38 |
| Formaldehyde | 27.96 | 7.877 | 11.96 | $3.22 \times 10^{-9}$ | 100 |
| Acetaldehyde | 4.853 | 4.680 | 4.971 | 3.610 | 27.4 |
| Propionaldehyde | 1.232 | 0.426 | 1.259 | 1.064 | 15.48 |
| Acetone | 4.877 | 1.060 | 4.907 | 2.990 | 39.06 |
| Methanol | 13.91 | 9.118 | 11.01 | $2.54 \times 10^{-8}$ | 100 |
| Methylethyl-ketone | 3.960 | 0.376 | 4.013 | 3.217 | 19.84 |

That which is claimed is:

1. A process for the removal of oxygenate from an olefin rich gas stream, the process comprising the steps of:
    (a) reacting an oxygenate feedstock, comprising oxygenate, in an oxygenate reaction zone in the presence of a catalyst comprising a molecular sieve, at a temperature in the range of from 350 to 1000° C., to produce a reaction effluent stream, comprising at least oxygenate, olefin, water and acidic by-products;
    (b) cooling the reaction effluent stream and contacting it with a first aqueous stream in a quench zone to produce an aqueous stream and an olefin rich gas stream;
    (c) compressing the olefin rich gas stream in one or more compressors in series to produce a compressed gas stream,
    (d) cooling the compressed gas stream and separating condensed material from said gas stream after each of the one or more compressors,
    wherein after at least one of the one or more compressors in step (c), step (d) is carried out by contacting the compressed gas stream directly with a second aqueous stream in a conduit transporting the compressed gas stream from one compressor to another compressor and separating the resultant material into an oxygenates depleted gas stream and an aqueous wash stream.

2. The process of claim 1, wherein step (d) is carried out after one of the one or more compressors.

3. The process of claim 1, wherein step (d) is carried out by contacting the compressed gas stream directly with a second aqueous stream and separating the resultant material into an oxygen depleted gas stream and an aqueous wash stream when the compressed gas stream has been compressed to a pressure in the range of from 9 to 15 bar absolute (900 to 1500 kPa).

4. The process of claim 3, wherein step (d) is carried out by contacting the compressed gas stream directly with a second aqueous stream and separating the resultant material into an oxygen depleted gas stream and an aqueous wash stream when the compressed gas stream has been compressed to a pressure in the range of from 10 to 12 bar absolute (1000 to 1200 kPa).

5. The process of claim 1, wherein the second aqueous stream contains less than 10 ppm of oxygenates before it is contacted with the compressed gas stream.

6. The process of claim 5, wherein the second aqueous stream contains less than 1 ppm of oxygenates before it is contacted with the compressed gas stream.

7. The process of claim 1, wherein the oxygenates depleted gas stream is subsequently treated with a caustic solution.

8. The process of claim 1, wherein step (d) is carried out by contacting the compressed gas stream directly with a second aqueous stream and separating the resultant material into an oxygen depleted gas stream and an aqueous wash stream in a column containing trays or packing.

9. The process of claim 1, wherein the compressed gas stream is brought into with the second aqueous stream in a counter current fashion.

* * * * *